(12) United States Patent
Nielsen et al.

(10) Patent No.: US 11,419,504 B2
(45) Date of Patent: Aug. 23, 2022

(54) METHODS AND SYSTEMS FOR COMBINATION ELECTRODES FOR WEARABLE DEVICES

(71) Applicant: Fitbit, Inc., San Francisco, CA (US)

(72) Inventors: Jens Mitchell Nielsen, San Francisco, CA (US); Jaclyn Leverett Wasson, Alameda, CA (US); Kyung Nim Noh, San Francisco, CA (US); Man-Chi Liu, San Francisco, CA (US); Alan Luu, San Francisco, CA (US); Peter Colin Dess, San Francisco, CA (US); Lindsey Michelle Sunden, San Francisco, CA (US); Lukas Bielskis, San Francisco, CA (US); Thomas Consolazio, San Francisco, CA (US); Steven Thomas Woodward, San Francisco, CA (US); Dennis Jacob McCray, San Diego, CA (US)

(73) Assignee: FITBIT, INC., San Francisco, CA (US)

(*) Notice: Subject to any disclaimer, the term of this patent is extended or adjusted under 35 U.S.C. 154(b) by 15 days.

(21) Appl. No.: 16/457,363

(22) Filed: Jun. 28, 2019

(65) Prior Publication Data

US 2020/0405160 A1    Dec. 31, 2020

(51) Int. Cl.
| | | |
|---|---|---|
| *A61B 5/0205* | (2006.01) | |
| *H05K 5/00* | (2006.01) | |
| *H05K 5/02* | (2006.01) | |
| *G01K 1/14* | (2021.01) | |
| *G01J 1/02* | (2006.01) | |
| *A61B 5/00* | (2006.01) | |
| *A61B 5/282* | (2021.01) | |

(52) U.S. Cl.
CPC ........ *A61B 5/02055* (2013.01); *G01J 1/0271* (2013.01); *G01K 1/14* (2013.01); *H05K 5/0086* (2013.01); *H05K 5/0247* (2013.01); *A61B 5/0008* (2013.01); *A61B 5/282* (2021.01); *A61B 5/681* (2013.01); *A61B 2560/0456* (2013.01); *G01J 2001/0257* (2013.01)

(58) Field of Classification Search
CPC ... A61B 5/02055; A61B 5/0008; A61B 5/681; A61B 2560/0456; H05K 5/0247; H05K 5/0086; G01K 1/14; G01J 1/0271
See application file for complete search history.

(56) References Cited

U.S. PATENT DOCUMENTS

| | | | |
|---|---|---|---|
| 5,613,495 A * | 3/1997 | Mills .................... | A61B 5/7207 600/509 |
| 9,581,972 B1 * | 2/2017 | Arrow .................... | G06F 1/163 |

(Continued)

OTHER PUBLICATIONS

International Preliminary Report on Patentability for Application No. PCT/US2020/035562, dated Jan. 6, 2022, 7 pages.

*Primary Examiner* — Brian T Gedeon
*Assistant Examiner* — Joshua Andrew Schum-Houck
(74) *Attorney, Agent, or Firm* — Dority & Manning, P.A.

(57) ABSTRACT

Various embodiments provide a wellness tracking device with a base plate that may be utilized as a combination electrode by a variety of sensors. The base plate may be a multi-material electrode that includes a conductor and a transparent or semi-transparent material to enable optical sensing. In certain embodiments, the base plate supports a plurality of different sensors, which may selectively utilize the base plate as an electrode.

20 Claims, 11 Drawing Sheets

(56) References Cited

U.S. PATENT DOCUMENTS

| | | |
|---|---|---|
| 10,307,101 B1* | 6/2019 | Miller .................. A61B 5/1455 |
| 2015/0346766 A1 | 12/2015 | Justice et al. |
| 2016/0166197 A1 | 6/2016 | Venkatraman et al. |
| 2017/0195584 A1* | 7/2017 | Kostrzewa ........... H04N 5/2253 |
| 2018/0256101 A1* | 9/2018 | Li ........................ A61B 5/0024 |
| 2018/0353134 A1 | 12/2018 | Walter et al. |
| 2019/0045642 A1* | 2/2019 | Prest ..................... H05K 5/006 |
| 2019/0072912 A1* | 3/2019 | Pandya ................ G04G 9/0005 |
| 2019/0110744 A1* | 4/2019 | Zhu .................... A61B 5/02055 |

* cited by examiner

METHODS AND SYSTEMS FOR COMBINATION ELECTRODES FOR WEARABLE DEVICES

BACKGROUND

Wearable electronic devices have gained popularity among consumers. A wearable electronic device may track a user's activities using a variety of sensors. Data captured from these sensors can be analyzed in order to provide a user with information, such as an estimation of how far they walked in a day, their heart rate, how much time they spent sleeping, and the like. However, wearable devices may have limited surfaces areas where sensors may be arranged, and moreover, the position of the various sensors may impact the accuracy of the readings. Increasing the size of the wearable devices may not be feasible for a variety of reasons.

BRIEF DESCRIPTION OF THE DRAWINGS

Various embodiments in accordance with the present disclosure will be described with reference to the drawings, in which.

DETAILED DESCRIPTION

Figure 1:
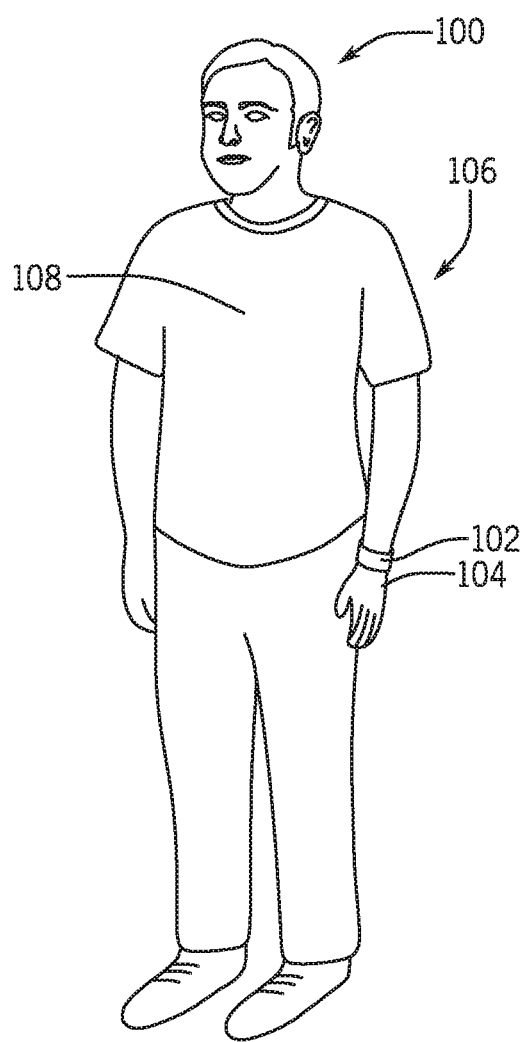
FIG. 1 illustrates an example of a user with a wearable device on an extremity, in accordance with various embodiments of the present disclosure.

In the following description, various embodiments will be described. For purposes of explanation, specific configurations and details are set forth in order to provide a thorough understanding of the embodiments. However, it will also be apparent to one skilled in the art that the embodiments may be practiced without the specific details. Furthermore, well-known features may be omitted or simplified in order not to obscure the embodiment being described. Incorporated by reference, in their entireties, are "INTEGRATED ECG ELECTRODE AND ANTENNA RADIATOR," filed Jun. 28, 2019, which claims priority to and the benefit of U.S. Provisional Patent Application No. 62/697,844, titled "INTEGRATED ECG ELECTRODE AND ANTENNA RADIATOR," filed Jul. 13, 2018.

Systems and methods in accordance with various embodiments of the present disclosure may overcome one or more of the aforementioned and other deficiencies experienced in conventional approaches for wearable devices, such as electronic wellness trackers. In particular, various embodiments provide a wearable device with a base plate that functions to enable a variety of sensors to receive information from a user wearing the wearable device. The base plate may be formed to have a surface area that enables multiple sensors to obtain information while maintaining a form factor of the wearable device. In certain embodiments, the base plate is a multi-material electrode that includes a conductor (e.g., thermally conductive, electrically conductive) and a transparent or semi-transparent material to enable optical sensing. As used herein, transparent or semi-transparent refers to a material that allows light to pass through. As will be appreciated, a transparent material will allow more light to pass through than a semi-transparent material. Accordingly, embodiments of the present disclosure include a base plate that may be utilized with a variety of sensors for obtaining health information from a user of a wearable device.

In various embodiments, the base plate may be utilized with a skin temperature sensor. For example, the base plate may be formed from a thermally conductive material that, over time, may reach equilibrium or substantial-equilibrium with a contact surface (e.g., skin). The base plate may be coupled to a temperature sensor, which may record the temperature of the base plate as representative of the contact surface. In certain embodiments, the base plate may have a surface area larger than a threshold amount, for example larger than a contact between the sensor and the base plate, to thereby provide an average temperature of the contact surface over the surface area of the base plate. That is, the base plate may include a larger surface area to enable averaging of the heterogeneous nature of the contact surface, such as skin, to determine a surface temperature. In various embodiments, this surface temperature may be correlated with other temperatures, such as an ambient temperature or a core body temperature, to provide health and wellness information to a user.

FIG. 1 illustrates an example of a user 100 wearing a user monitoring device 102 around a wrist 104 of the user 100. The user monitoring device 102 may also be referred to as a wearable or a fitness tracker, and may also include devices that are worn around the chest, legs, head, or other body part, or a device to be clipped or otherwise attached onto an article of clothing worn by the user 100. The user monitoring device 102 may collectively or respectively capture data related to any one or more of caloric energy expenditure, floors climbed or descended, heart rate, heart rate variability, heart rate recovery, location and/or heading (e.g., through GPS), elevation, ambulatory speed and/or distance traveled, swimming lap count, bicycle distance and/or speed, blood pressure, blood glucose, skin conduction, skin and/or body temperature, electromyography data, electroencephalographic data, weight, body fat, respiration rate and patterns, various body movements, among others. Additional data may be provided from an external source, e.g., the user may input their height, weight, age, stride, or other data in a user profile on a fitness-tracking website or application and such information may be used in combination with some of the above-described data to make certain evaluation or in determining user behaviors, such as the distance traveled or calories burned of the user. The user monitoring devices may also measure or calculate metrics related to the environment around the user such as barometric pressure, weather conditions, light exposure, noise exposure, and magnetic field.

In some embodiments, the user monitoring device 102 may be connected to a network directly, or via an intermediary device. For example, the use monitoring device 102 may be connected to the intermediary device via a BLUETOOTH® connection, and the intermediary device may be connected to the network via an Internet connection. In various embodiments, a user may be associated with a user account, and the user account may be associated with (i.e., signed onto) a plurality of different networked devices. In some embodiments, additional devices may provide any of the abovementioned data among other data, and/or receive the data for various processing or analysis. The additional devices may include a computer, a server, a handheld device, a temperature regulation device, or a vehicle, among others. Thus, the game state may be determined based on a combination of data collected from these devices.

In the illustrated embodiment, the user monitoring device 102 may include a skin temperature sensor. The skin temperature sensor may be used to determine various pieces of health information about the user, such as whether the user is sleeping (e.g., due to a drop in body temperature), whether the user is exercising or ill (e.g., due to an increase in body temperature), whether the user is at risk for overheating (e.g., due to a measurement of temperature above a threshold), and the like. However, a direct measurement of the wrist on an extremity 106 may be different than a measurement of a core 108. For example, from a physiological perspective, a human body may preferentially preserve heat within the core 108 than the extremity 106. As a result, a determination of core body temperature from a measurement on an extremity may be difficult to obtain.

Moreover, a surface area of the extremity 106 may be small and therefore provide a localized temperature rather than a generalized temperature over the area. This may lead to a false reading, as human skin, for example, is heterogeneous. That is, a sensor arranged over a vein may provide a different reading than a sensor placed over a bone. Furthermore, different areas of the skin may be exposed to ambient temperatures differently. As a result, a small, individualized sensor with a small contact area may be insufficient to determine the skin temperature of the user 100. As will be described below, embodiments of the present disclosure include a base plate to enable skin temperature sensing over a larger surface area, thereby providing an improved temperature measurement.

Figure 2A:
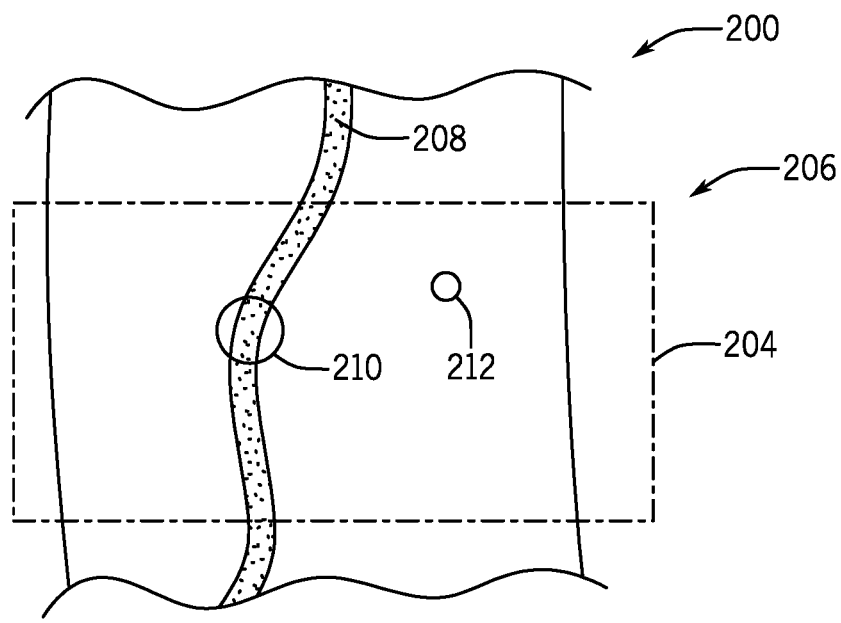
FIG. 2A illustrates a schematic top plan view of an embodiment of a wearable device arranged on an extremity, in accordance with various embodiments of the present disclosure.
Figure 2B:
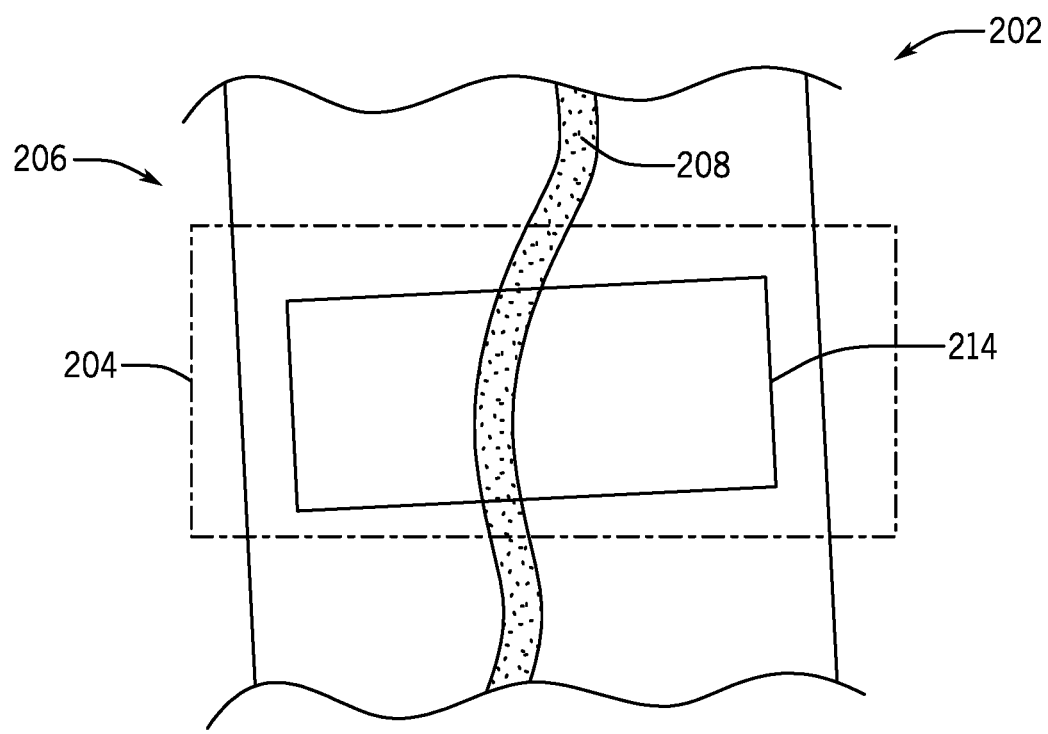
FIG. 2B illustrates a schematic top plan view of an embodiment of a wearable device arranged on an extremity, in accordance with various embodiments of the present disclosure.

FIGS. 2A and 2B are graphical representations of examples of environments 200, 202 including wearable devices 204 arranged along an extremity 206, such as a wrist. In the illustrated embodiment, the wearable devices 204 are positioned over an area of the extremity 206 including a vein 208. As described above, a location of any sensor for determining skin temperature may be effected by properties of the skin, since skin is heterogeneous and different skin areas may be different temperatures for a variety of reasons. The environment 200 includes the wearable device 204 that includes, by way of example only, two sensors 210, 212. It should be appreciated that the sensors referred to with respect to FIG. 2A may include contacts and/or electrodes that have a surface area substantially equal to the size of the sensors 210, 212. That is, the electrodes that receive the signal (e.g., temperature) from the skin are at localized points, as illustrated in FIG. 2A. In the illustrated embodiment, sensor 210 will likely have different reading than sensor 212 because the vein 208 is arranged below the sensor 210 while the sensor 212 receives information from a side of the extremity 206. Accordingly, information obtained by the sensors 210, 212 may be inaccurate, thereby reducing the effectiveness of the information provided by the wearable device 204 to the user.

In the embodiment illustrated in FIG. 2B, an electrode 214 has a larger surface area than the sensors 210, 212. Accordingly, the electrode 214 extends over a larger portion of the wrist and, as a result, can obtain an average or equilibrium reading of the extremity 206. For example, the wearable device 204 may include circuitry and the like to evaluate a temperature of the electrode 214 (e.g., a gradient) to determine whether equilibrium has been reached over the electrode 214. Equilibrium may be defined as substantial equilibrium between regions of the electrode (e.g., a gradient differing by less than a threshold amount), a review of a change in temperature over a time being below a threshold amount, or the like. Accordingly, temperature information for the electrode 214 may account for various regions of the extremity 206, such as areas that include the vein 208 and those that do in. In this manner, an improved reading may be obtained utilizing the larger surface area. As will be described below, the electrode 214 may also be utilized in combination with one or more other sensors to determine biometric information.

Figure 3A:
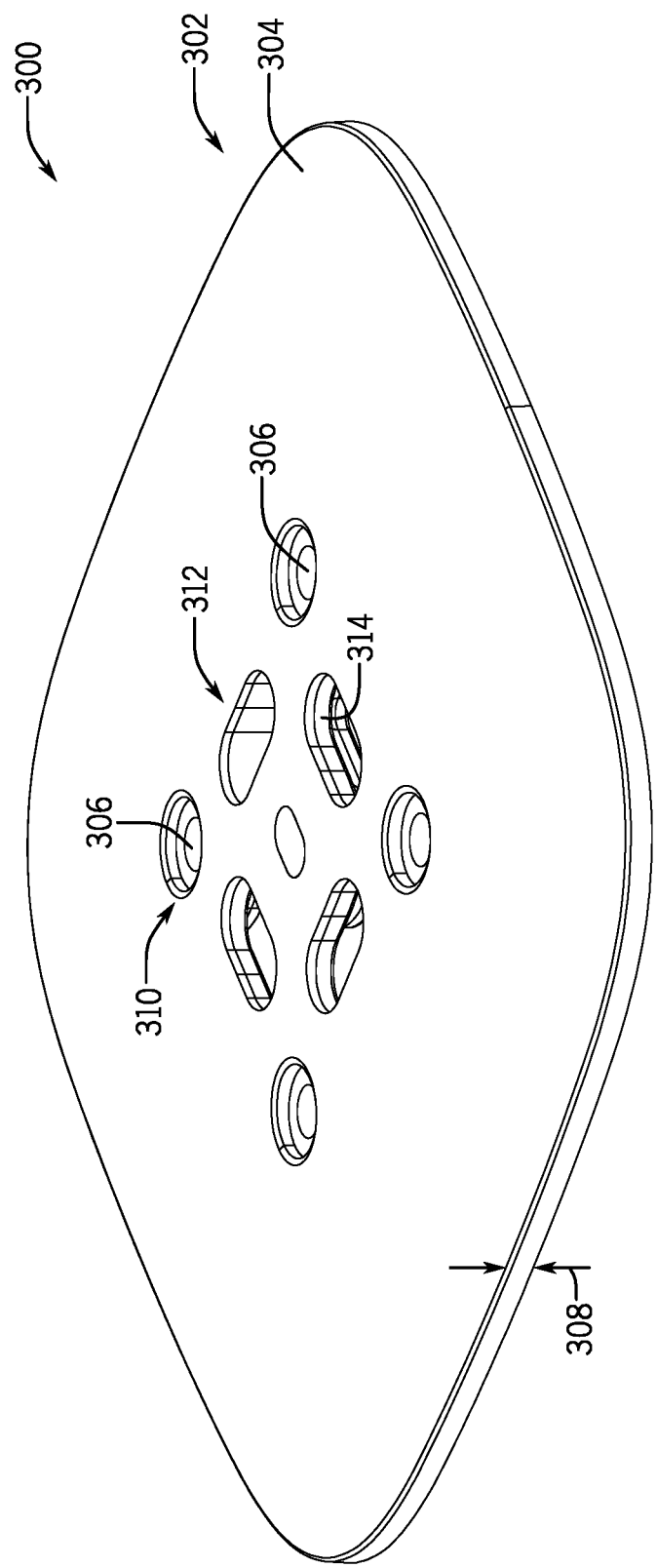
FIG. 3A illustrates a bottom perspective view of an embodiment of a base plate of a wearable device, in accordance with various embodiments of the present disclosure.

FIG. 3A is a top perspective view of an embodiment of a base plate 300, which may also be referred to as a combination electrode, and may be used with embodiments of the present disclosure. It should be appreciated that, in describing various features of the base plate, that phrases such as "top" or "bottom" are with respect to the illustrated embodiment and are not intended to limit the disclosure. For example, in various embodiments, a "bottom" or "outside" portion of the base plate 300 may be used to refer to a region that contacts a user (e.g., that is positioned against a user or clothing of the user). Furthermore, the use of "plate" does not necessarily mean that the base plate 300 is flat or substantially flat. Indeed, the base plate 300 may be arcuate, for example, to conform to an extremity of the human body, such as a wrist. Furthermore, various parts of the base plate 300 may be curved and/or flat. For example, a central portion may be substantially flat while the ends are curved to force around an arcuate area of the human body. The illustrated base plate 300 includes an outside surface 302 having a contact surface area 304 that may, in operation, be arranged in contact with an extremity of a user, such as along a wrist of the user. It should be appreciated that the entirety of the surface area 304 may not be in contact with the user due to the shape and/or size of the user's extremities.

The illustrated base plate 300 includes charging pins 306 recessed into a thickness 308 of the base plate 300. The charging pins 306 are illustrated as circular, however, may be any reasonable shape. Moreover, the charging pins 306 may not be recessed in other embodiments, but may be flush with the outside surface 302. As will be described below, the charging pins 306 may be formed of Niobium and include sleeves 310 of a different material, such as copper, brass, stainless steel, or the like. The charging pins 306 may be used to provide electrical energy to one or more components of the device, such as to an on-board battery.

The illustrated base plate 300 further includes openings 312 (e.g., windows) extending through the thickness 308. The illustrated openings 312 are apertures that extend entirely through the thickness 308. In various embodiments, the openings 312 may include a pane 314 (e.g., an insert), such as a plastic, glass, or the like. The pane 314 may be a transparent or semi-transparent material that may enable one or more sensors to obtain biometric information. For example, in embodiments, the sensors may include SpO2 sensors, PPG sensors, ECG sensors, temperature sensors, and the like. For example, the transparent or semi-transparent material of the pane 314 may enable a light to shine onto the skin of the user to changes in light absorption. In certain embodiments, the pane 314 is formed from a material different than the base plate 300. For example, the base plate 300 may be metallic while the pane 314 is glass. Accordingly, material properties for the base plate 300 and/or the pane 314 may be particularly selected to accommodate for differences in coefficients of thermal expansion, manufacturing processes, and the like.

In various embodiments described herein, the base plate 300 may be referred to with respect to one or more sensors where the base plate 300 provides one or more electrical contacts for the one or more sensors. In certain embodiments, the base plate 300 may be representative of a single, continuous contact. However, in various embodiments, the base plate 300 may represent multiple electrical contacts, for example, by dividing the base plate 300 into different segments. By way of example only, half of the base plate 300 may provide an electrode for one or more sensors while a second half of the base plate 300 may provide an electrode for one or more other sensors. Additionally, the first half of the base plate 300 may provide a first electrical contact for a first sensor while the second half of the base plate 300 may provide a second electrical contact for the first sensor. Accordingly, while embodiments of the present disclosure may refer to the base plate 300 as a singular contact, it should be appreciated that the base plate 300 may be segmented to provide various electrical contacts and that one or more sensors may receive input signals from one or more segments of the base plate 300.

Figure 3B:
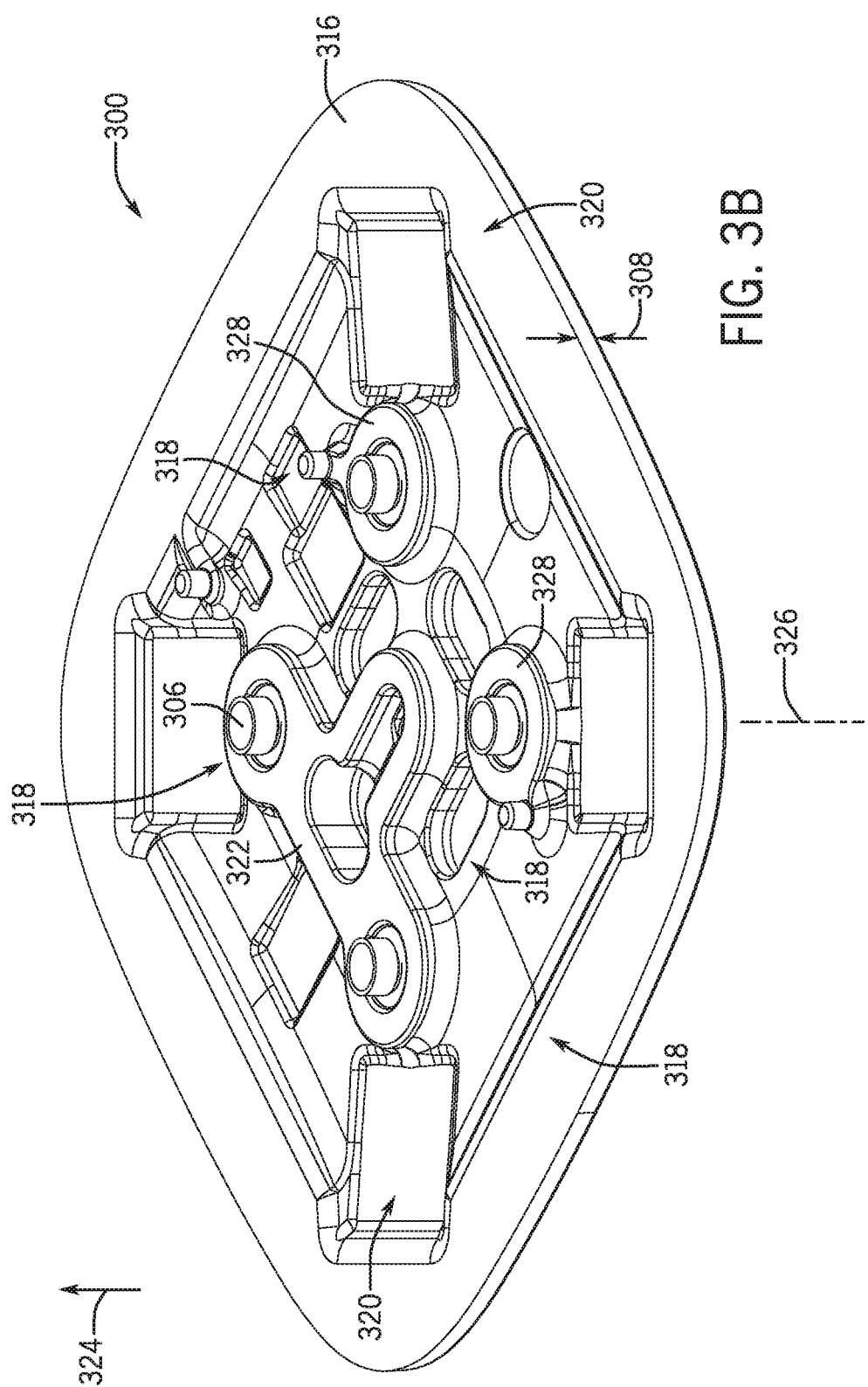
FIG. 3B illustrates a top perspective view of an embodiment of a base plate of a wearable device, in accordance with various embodiments of the present disclosure.

FIG. 3B is a top perspective view of an embodiment of the base plate 300 illustrating an opposite side as illustrated in FIG. 3A. The illustrated base plate 300 includes an inside surface 316, which is opposite the outside surface 302. For example, the illustrated inside surface 316 may be arranged within a body of a wearable device, such as a fitness tracker, and therefore may not be in contact with a user during normal operating conditions.

The illustrated inside surface 316 includes a plurality of recesses 318. The illustrated recesses 318 have different shapes and depths, which may be particularly selected for particular conditions and/or components. For example, in various embodiments, coupling recesses 320 may receive magnets (not pictured), which may be used to facilitate coupling the base plate 300, and as a result the wearable device, to a charger, stand, or the like. For example, in certain embodiments the base plate 300 may be formed from a non-ferrous material, such as 316L stainless steel. By providing separate magnets, magnetic coupling may be utilized, which may facilitate snapping or coupling of the wearable device and improve user interaction with the device.

In the illustrated embodiment, the coupling recesses 320 are arranged substantially symmetrically. That is, there is one coupling recess 320 at each corner location of the inside surface 316. However, it should be appreciated that, in other embodiments, the coupling recesses 320 may not be symmetrical. Moreover, the coupling recesses 320 may not be arranged at the corners. For example, the coupling recesses 320 may be arranged longitudinally along the sides of the coupling recesses 320, which could be arranged to enable magnetic coupling. Accordingly, it should be appreciated that various locations or dimensions of the features of the inside surface 316 are shown for illustrative purposes only and are not intended to limit the scope of the disclosure.

Further illustrated in the embodiment illustrated in FIG. 3B is a platform 322 that includes mounting locations for the charging pins 306. The illustrated platform 322 includes two charging pins 306 and further includes the opening 312 extending through the thickness 308 of the base plate 300. The charging pins 306 extending normal to the platform 322 in a first direction 324 substantially parallel to an axis 326 of the base plate 300. It should be appreciated that a distance of extension of the charging pins 306 may be particularly selected for a number of reasons, such as clearance space, size of the wearable device, and the like.

In various embodiments, secondary platforms 328 are arranged proximate other charging pins 306. As a result, the charging pins 306 may be positioned at a higher elevation, relative to the inner surface 316, than the recesses 320. Various other secondary recesses 330 may further be included on the inner surface 316. The size and location of the secondary recesses 330 may be particularly selected for certain components. For example, various sensors or chips may be arranged within the secondary recesses 330 to provide a mounting location and reduce the likelihood of movement of the sensors.

Figure 4:
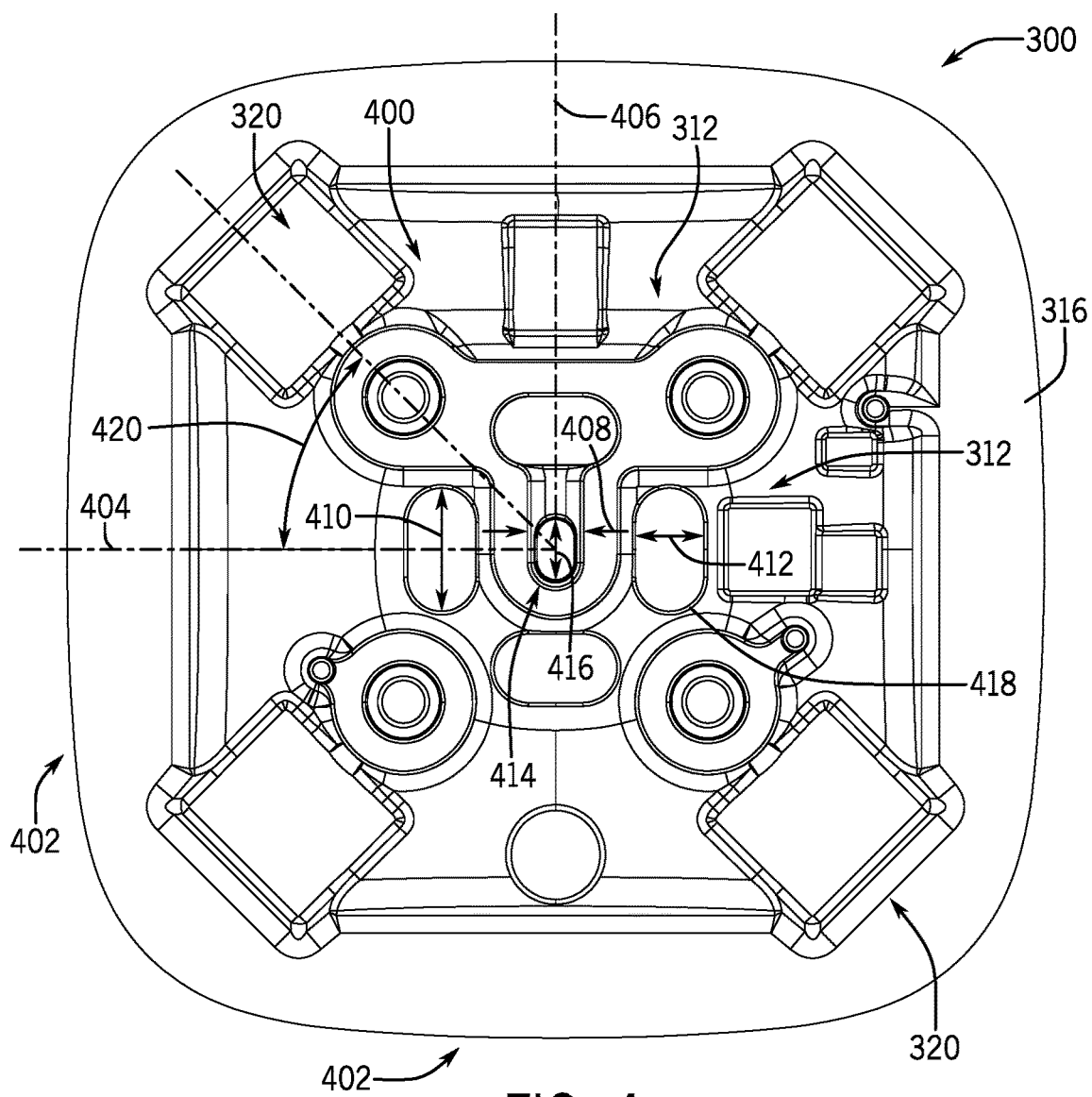
FIG. 4 illustrates a top plan view of an embodiment of a base plate of a wearable device, in accordance with various embodiments of the present disclosure.

FIG. 4 is a top plan view of the base plate 300 illustrating the inside surface 316. It should be appreciated that like reference numerals may be used between figures for convenience and that the use of like reference numerals is not intended to limit the scope of the disclosure. As described above, variations in height (e.g., depth relative to an axis of the base plate 300) may be distributed across different areas of the base plate 300. These variations may enable different components to be positioned closer to or further away from the extremity where the base plate 300 is positioned. In the illustrated embodiment, the openings 312 are arranged proximate central area 400 of the base plate 300. Location in the central area 400 may provide various advantages, such as reducing a likelihood of variation due to effects at the edges 402 of the base plate 300. For example, the edges 402 may have various temperature gradients or changes due to greater exposure to environmental conditions (e.g., wind) than the central area 400. The illustrated openings 312 are positioned to be substantially symmetrical with respect to a horizontal axis 404 and a vertical axis 406. The horizontal axis 404 may be referred to as the x-axis while the vertical axis 406 may be referred to as the z-axis. It should also be appreciated that the axis 326 may be referred to as the y-axis.

The openings 312 illustrated in FIG. 4 are substantially pill shaped. That is, the openings 312 have a substantially rectangular shape with curved edges 408. The pilled shaped openings 312 are for illustrated purposes only, and in various embodiments 312 may be different shapes, such as circles, rectangles, squares, or any other reasonable shape. Furthermore, each of the openings 312 may not be the same shape. For example, some openings 312 may be pill shaped while other windows are rectangular or circular. In the illustrated embodiment, the openings 312 have a length 410 and a width 412. In certain embodiments, the ratio of the length 410 to the width 412 may be approximately 1.8, which provides a 1.8:1 aspect ratio. However, this for illustrative purposes only and different opening shapes may provide different aspect ratios. That is, the aspect ratio may be particularly selected based on a size of the base plate 300 and/or a size of the sensors arranged to utilize the various openings 312.

Further illustrated in the embodiment of FIG. 4 is a central opening 414, which may be part of the openings 312, which is smaller than the other illustrated openings 312. For example, the central opening 414 includes a length 416 and a width 418. However, the illustrated central opening 414 has an aspect ratio of 1.6:1, which is smaller than the aspect ratio of the openings 312. However, as noted above, this is for illustrative purposes only and the aspect ratio of the central opening 414 maybe larger than or equal to the aspect ratio of one or more of the openings 312.

In various embodiments the coupling recesses 320 are arranged proximate the edges 402 and are substantially symmetrical about the horizontal axis 404 and the vertical axis 406. The illustrated coupling recesses 320 are arranged at an angle 420 with respect to the vertical axis 406. It should be appreciated that the angle 420 may be particularly selected based on various aspects, such as a size of the base plate 300 (e.g., a surface area), arrangement of the platforms 322, 328, and the like. In the illustrated embodiment, the various coupling recesses 320 extend proximate the platforms 322, 328. However, in other embodiments, a size of the coupling recesses 320 may be different such that the coupling recesses 320 do not extend proximate the platforms 322, 328.

Figure 5:
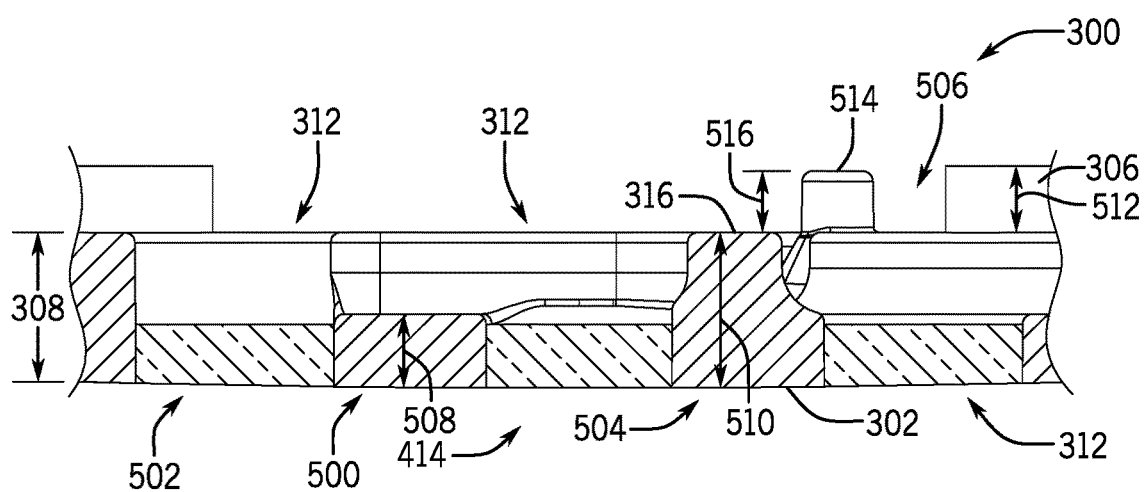
FIG. 5 illustrates a cross-sectional side elevation view of an embodiment of a base plate of a wearable device, in accordance with various embodiments of the present disclosure.

FIG. 5 is a cross-sectional side elevational view of an embodiment of the base plate 300. As illustrated, the base plate 300 includes the thickness 308, which extends from the outside surface 302 to the inside surface 316. The illustrated cross-sectional view extends through the openings 312 and the central opening 414 (e.g., along the horizontal axis 404). The openings 312 extend through the thickness 308, thereby providing optical access to through the base plate 300, for example, for one or more sensors. As will be described herein, the base plate 300 may be utilized to position one or more sensors to proximate an extremity as well as acting as an electrode for one or more sensors.

A transition 500 is arranged between a first opening 502 and the central opening 414. Furthermore, a barrier 504 is arranged between a second opening 506 and the central opening 414. The transition 500 has a first height 508, which is less than a second height 510, which is equal to the thickness 308 in the illustrated embodiment. In various embodiments, the transition 500 and the barrier 504 may be utilized to separate or otherwise block various signals or transmission between different sensors. For example, various embodiments may emit light while other sensors may measure reflective light, and as a result, the emitted light may impact the measurement from the sensor that measures reflective light. Accordingly, the transition 500 and/or the barrier 504 enable various different sensors to be arranged closely on the base plate 300 while blocking or reducing the likelihood of interference between the various signals of the sensors.

Further illustrated are the charging pins 306 extending normal to the inside surface 316. The charging pins have a third height 512, which may be particularly selected based on various design considerations. Furthermore, FIG. 5 includes a pin 514. The pin 514 may be used as a spacer, for example, between an upper housing that may be coupled to the base plate 300. In the illustrated embodiment, the pin 514 has a fourth height 516, which is substantially equal to the third height 512 of the charging pins. However, it should be appreciated that the fourth height 516 may be larger than or smaller than the third height 512. In various embodiments, an arrangement of pins 514 on the base plate 300 may facilitate assembly, as the pins 514 may be utilized to align or otherwise position a housing over the base plate 300. It should be appreciated that, in other embodiments, one or more of the pins 514 may be utilized as ECG pins.

Figure 6A:
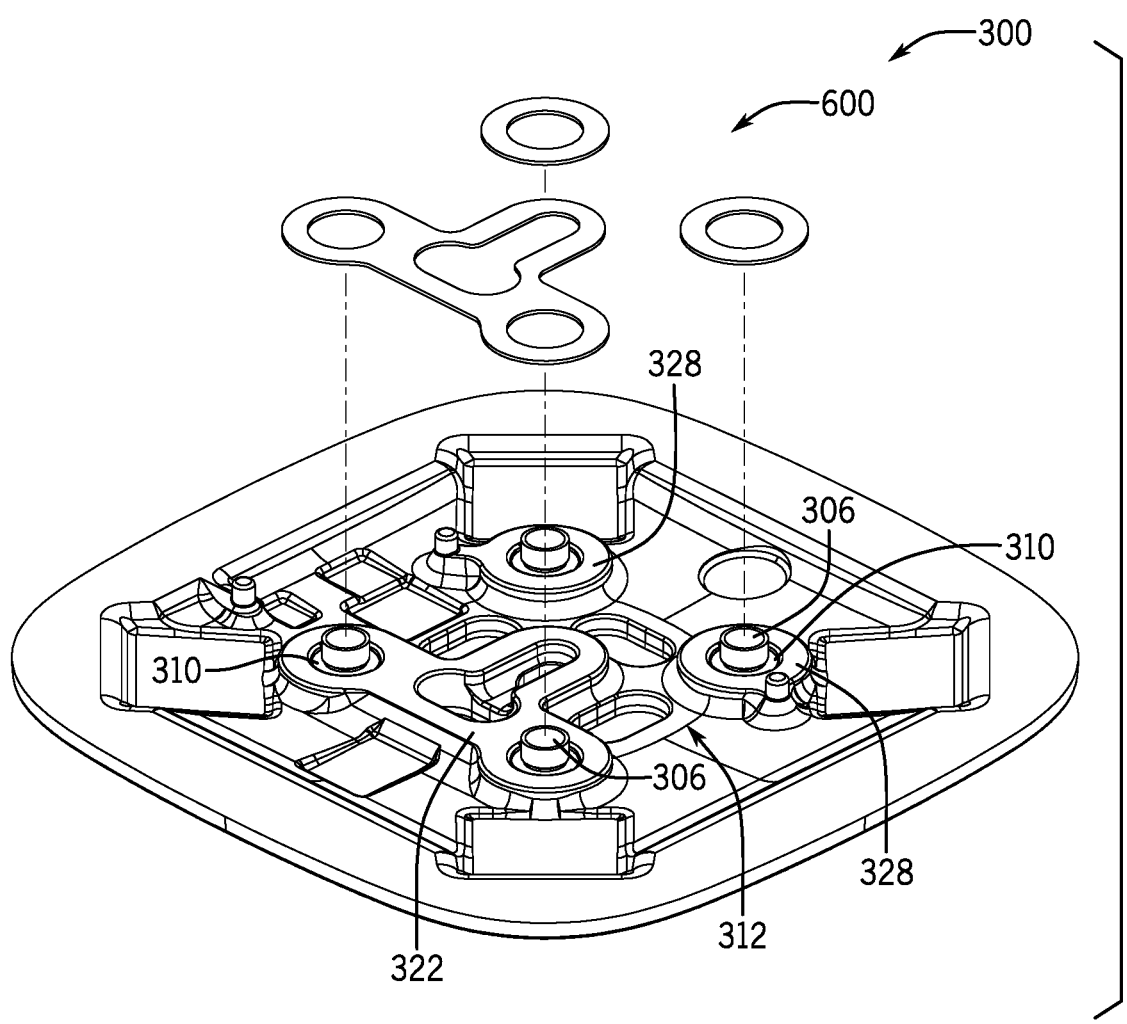
FIG. 6A illustrates a top exploded perspective view of an embodiment of a base plate and light blocking assembly of a wearable device, in accordance with embodiments of the present disclosure.

FIG. 6A is a top perspective exploded view of an embodiment of the base plate 300 including a light blocking assembly 600. In the illustrated embodiment, the light blocking assembly 600 is positioned to land on the platforms 322, 328. As described below, the platforms 322, 328 may receive the charging pins 306, which extend through the thickness 308 of the base plate 300. As a result, in various embodiments, light may leak through the openings (for example, between the openings and the sleeves 310), which may enter a housing of the wearable device, which may interact with one or more sensors. The interaction with the sensor may be undesirable and may lead to a false or otherwise incorrect reading. Accordingly, the light blocking assembly 600 may be utilized to keep the interior of the device substantially light tight. That is, the light within the housing may be limited or substantially limited to light entering through one or more of the openings 312.

Figure 6B:
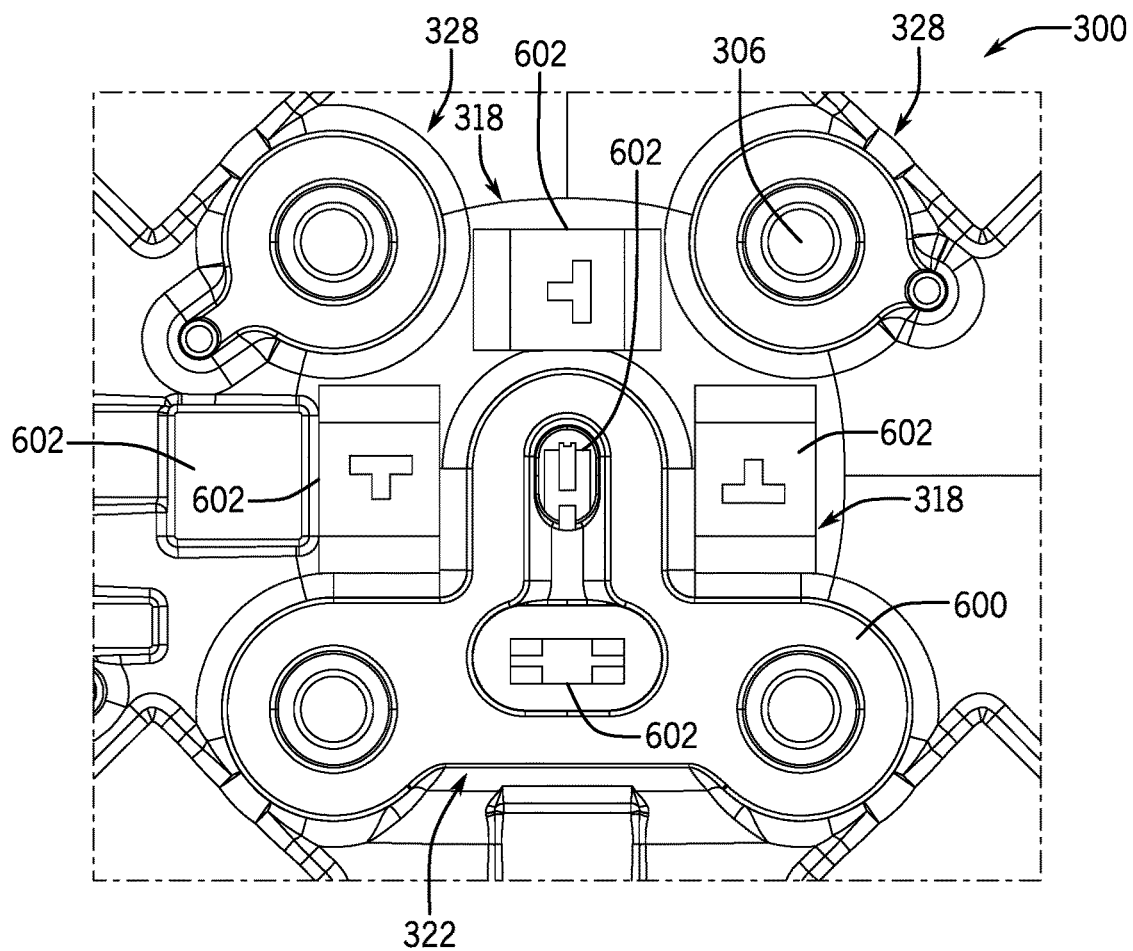
FIG. 6B is a top plan view of an embodiment of a base plate and light blocking assembly of a wearable device, in accordance with embodiments of the present disclosure.

FIG. 6B is a top plan view of an embodiment of the base plate 300 including the light blocking assembly 600 arranged on the platforms 322, 328. In various embodiments, the light blocking assembly 600 may include an adhesive on one side to facilitate coupling to the base plate 300. In the illustrated embodiment, the light blocking assembly 600 follows the respective contours of the platforms 322, 328. As a result, light entering through one or more openings through which the charging pins 306 extend may be substantially blocked.

The illustrated embodiment further includes a plurality of sensors 602. As noted above, the sensors 602 may include a plurality of different sensors, such as SpO2 sensors, PPG (photoplethysmography) sensors, ECG (electrocardiography) sensors, temperature sensors, and the like. By way of example, ECG is a process that can be used to determine and/or track the activity of the heart of a person over a period of time. In order to obtain ECG data, a conductive electrode, such as the base plate 300, is often brought into contact with the skin of the person to be monitored. In the illustrated embodiment, the sensors 602 are arranged within the recesses 318. Furthermore, the sensor 602 is arranged within a secondary recess 330, which may be a temperature sensor. In various embodiments, the recesses 318 are arranged over the openings 312 to facilitate alignment with the one or more openings 512. As will be appreciated, the recesses 318 may be sized to receive the sensors 602, and as a result, the dimensions of the recesses 318 may vary based on the sensors 602. The illustrated embodiment spaces the sensors 602 from one another, thereby facilitating heat transfer, but also arrangements the sensors 602 close enough to simplify wiring and other connection to one or more processors for evaluating information obtained from the sensors. Furthermore, one or more of the sensors 602 may utilize the base plate 300 as an electrode, as described above. Additionally, in various embodiments, the sensors 602 may be arranged within associated segments of the base plate 300, which may provide at least one electrical contact to the sensors 602. Furthermore, different segments of the base plate 300 may provide additional contacts to the sensors 602, as described above. Accordingly, the arrangement of the baseplate 300 facilitates the mounting and use of multiple different sensors 602 which may share a common electrode and/or multiple segments of the base plate 300.

Figure 7:
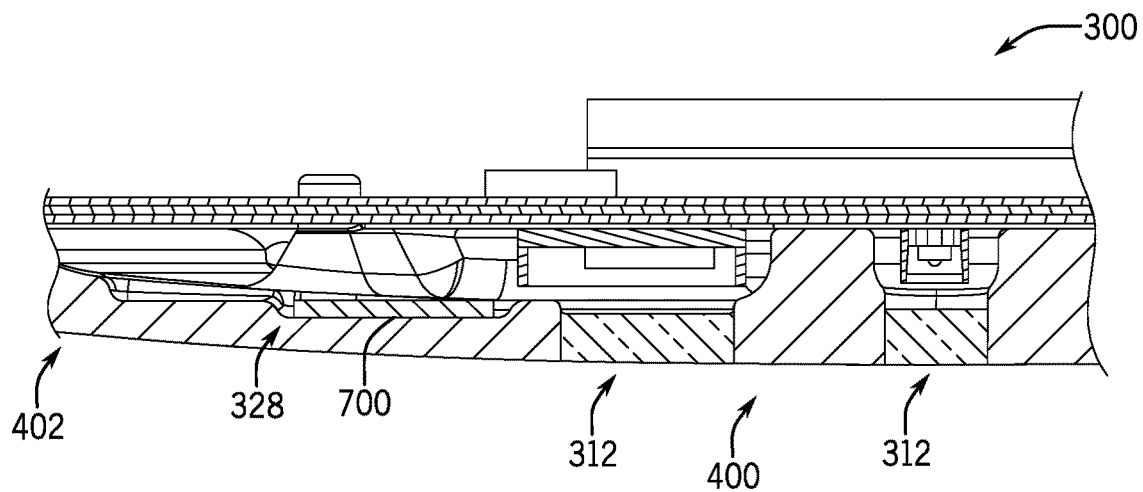
FIG. 7 illustrates a cross-sectional side elevation view of an embodiment of a base plate of a wearable device including a temperature sensor, in accordance with various embodiments of the present disclosure.

FIG. 7 is a cross-sectional side elevation view of an embodiment of the base plate 300 including a temperature sensor 700, which may be one of the sensors 602. In the illustrated embodiment, the temperature sensor 700 is in direct contact with the base plate 300, which may act as an electrode for the temperature sensor 700. For example, in operation, the base plate 300 may be in contact with an extremity of a human utilizing a wearable device including the base plate 300. Over a period of time, a temperature of the base plate 300 will come into substantial equilibrium with the extremity, although it should be appreciated that there may be a temperature gradient over the base plate 300 because the edges 402 may be exposed to more environmental factors than the central area 400. The temperature of the base plate 300 is transmitted to the temperature sensor 700, which may be used to measure a temperature of the extremity.

Figure 8:
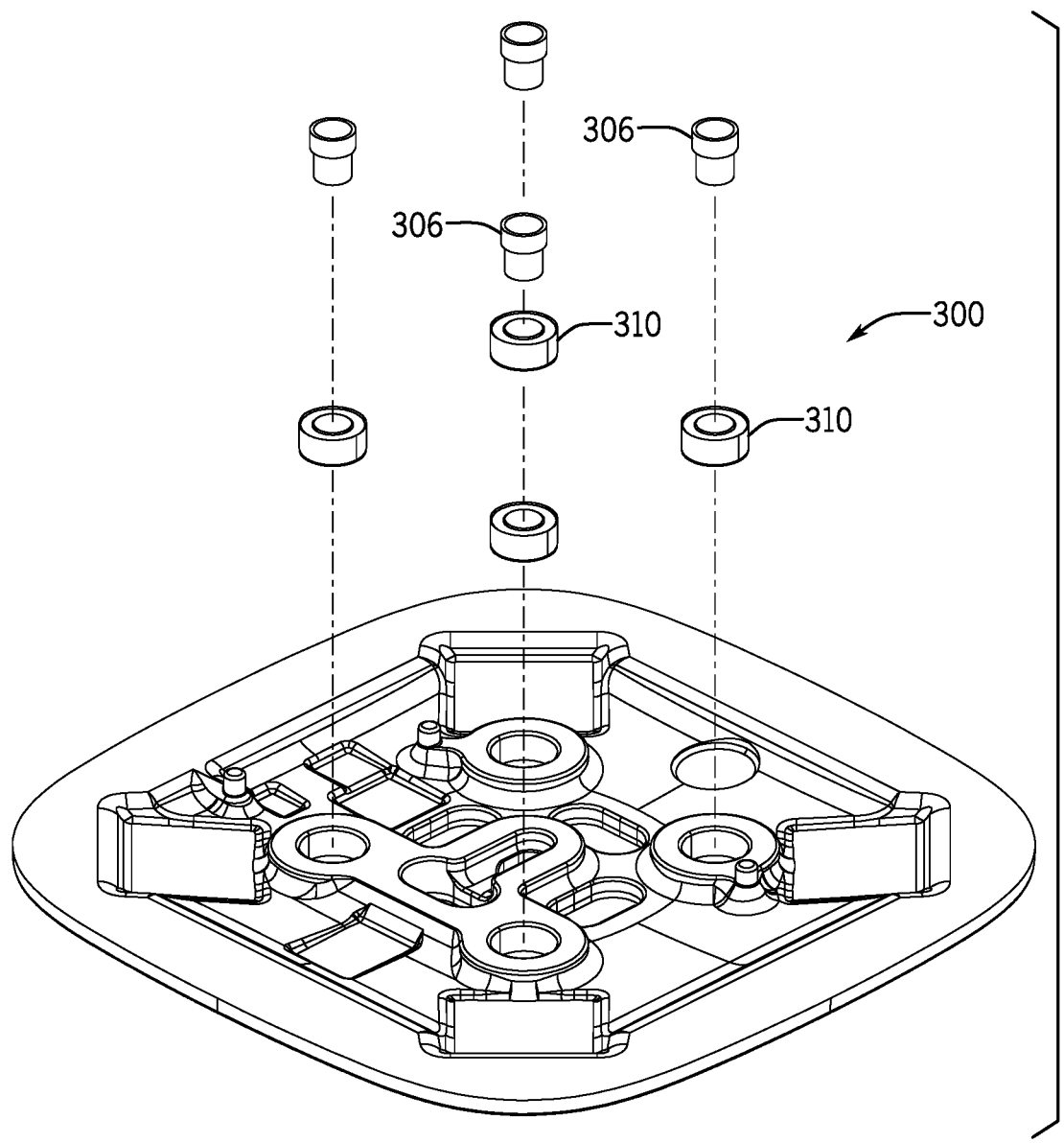
FIG. 8 illustrates a top exploded perspective view of an embodiment of a base plate and charging pins of a wearable device, in accordance with embodiments of the present disclosure.

FIG. 8 is an exploded perspective view of an embodiment of the base plate 300 illustrating the charging pins 306 including the sleeves 310. In various embodiments the changing pins 306 and the base plate 300 may be formed from different materials. For example, the base plate 300 may be stainless steel, such as 316L, while the charging pins may be niobium. As a result, it may be difficult to connect the base plate 300 to the charging pins 306, for example, via a soldering operation. Accordingly, the sleeves 310 may be coupled to the charging pins 306 to facilitate operation. The sleeves 310 may be formed from various different compatible materials, such as copper, brass, or a different grade of stainless steel. Moreover, in embodiments, a brazing operation, diffusion bond, or press-fit operation may be utilized to couple the sleeves 310 to the charging pins 306. Thereafter, the sleeves 310 may be soldered to the base plate 300. As a result, seemingly incompatible materials may be utilized with embodiments of the present disclosure.

Figure 9:
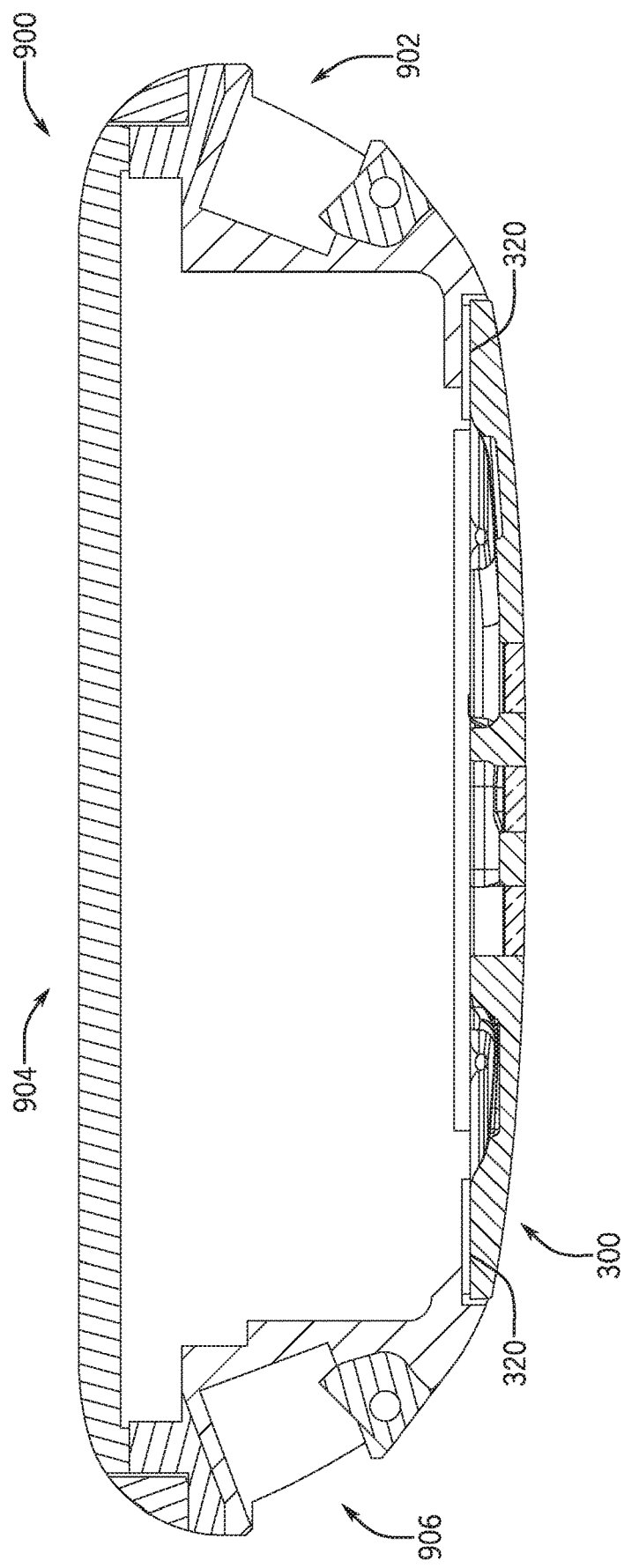
FIG. 9 illustrates a cross-sectional side elevation view of an embodiment of a housing of a wearable device, in accordance with embodiments of the present disclosure.

FIG. 9 is a cross-sectional side elevation view of an embodiment of a wearable device 900 that includes a housing 902 including an upper housing 904, a middle housing 906, and the base plate 300. The illustrated embodiment includes the coupling recesses 320 having magnets 908 to facilitate coupling of the middle housing 906 to the base plate 300. It should be appreciated that while the upper housing 904 and middle housing 906 may be labeled as separate components, in various embodiments a unitary design between the upper housing 904 and the middle housing 906 may be used. In various embodiments, one or more components of the middle housing 906 are formed from a ferrous material, or include a ferrous material, to facilitate coupling to the magnets 908. As such, assembly of the wearing device 900 may be simplified. It should be appreciated that, in various embodiments, additional coupling configurations may be utilized along with the illustrated magnetic coupling or in place of the illustrated magnetic coupling, such as fasteners, adhesives, clips, and the like. Furthermore, it should be appreciated that, for clarity, various components of the housing 902 have been removed, and their omission from the illustrated embodiment is not intended to limit or otherwise modify the scope of the present disclosure.

Figure 10:
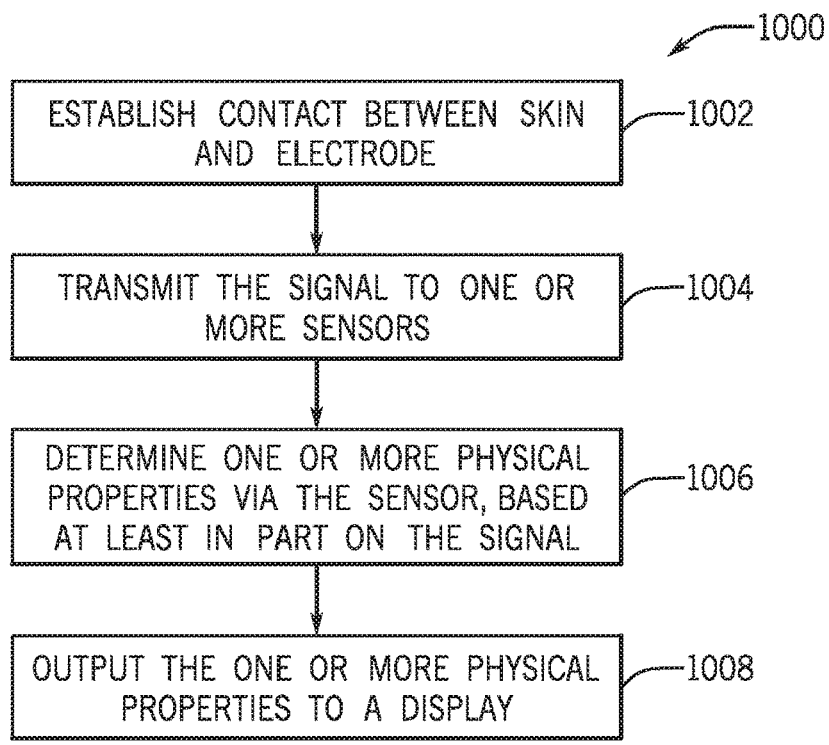
FIG. 10 illustrates an example process for determining a physical property of a user of a wearable device, in accordance with various embodiments of the present disclosure.

FIG. 10 is a flow chart of an example process 1000 for determining one or more physical properties of a user via a wearable device. It should be understood that, for any process discussed herein, there can be additional, fewer, or alternative steps performed in similar or alternative orders, or in parallel, within the scope of the various embodiments. In this example, the process starts by establishing contact between skin of a human extremity and an electrode 1002. For example, the electrode may form at least a portion of a wearable device that is worn against the skin of an extremity, such as on a wrist. The electrode may be metallic to enable transference of thermal and electric signals.

The process 1000 continues with a signal from the electrode transmitted to one or more sensors 1004. As noted herein, the signal may be a thermal signal or an electrical signal. For example, the signal may be a temperature of the skin that is transmitted to the electrode. Furthermore, in various embodiments, the signal may be an electrical signal transmitted from the skin through the electrode. One or more physical properties may be determined, based at least in part on the signal 1006. For example, the signal may be transmitted to one or more sensors, which may receive the signal and correlate the signal to one or more physical properties. For example, the temperature sensor may receive a signal indicative of a thermal temperature of the electrode and convert that signal to a temperature measurement. Also, in various embodiments, the electrical signal received from the electrode may also be utilized for conversion to a measurement of one or more physical properties.

In certain embodiments, the one or more physical properties may be transmitted to a display 1008. The display may provide information to a user wearing the wearable device, such as indication of extremity temperature, heart rate, and the like. In other embodiments, the information may be stored and/or transmitted to a server, for example a remote server, for tracking purposes. In this manner, an electrode formed in a wearable device may be utilized to determine one or more physical properties of a user.

Figure 11:
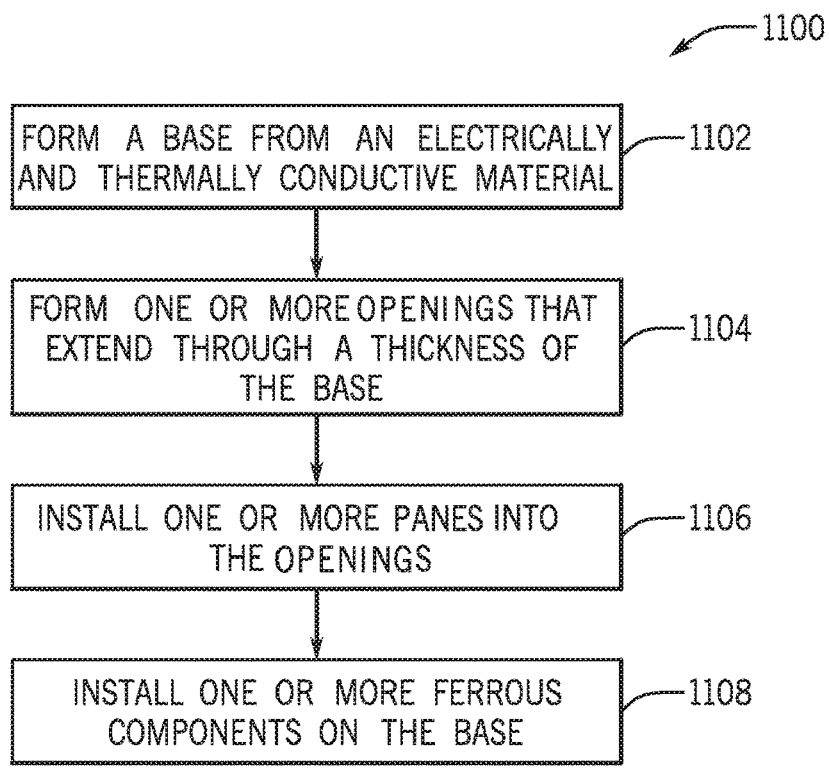
FIG. 11 illustrates an example process for forming a base plate of a wearable device, in accordance with various embodiments of the present disclosure.

FIG. 11 is a flow chart of an example process 1100 for manufacturing a wearable device base that may be used as a common electrode and/or provide electrodes for one or more sensors. In this example, the base is formed from an electrically and thermally conductive material 1102. For example, the base may be a metallic material, which may be ferrous or non-ferrous. In various embodiments, forming the base includes machining or otherwise processing (e.g., pressing) one or more features, such as the platforms, recesses, and the like described herein. One or more opening may be formed through the base 1104. The opening may provide an optical connection between an interior side of the base and an exterior side of the base. That is, the one or more opening may be described as apertures that extend entirely through the base to allow passage through a thickness of the base.

In various embodiments, one or more panes are installed inside the openings 1106. The one or more panes may be transparent or semi-transparent and may be formed from a different material than the base. For example, the panes may be a glass or plastic material while the base is a metallic material. In various embodiments, the materials forming the panes and the base may be particularly selected to have a substantially similar thermal expansion coefficient. The pane may be press fit, adhered, or otherwise installed within the openings. In various embodiments, the panes enable optical detection through the openings while blocking the ingress of environmental features, such as dust or debris, from entering an interior of a wearable device housing.

The example process also includes installing one or more ferrous components on the base 1108. The ferrous components may be utilized to form a magnetic closure between components of a wearable device housing. In various embodiments, the base may be ferrous, and as a result, the base may serve as the one or more ferrous components. However, in other embodiments, the base may be non-ferrous, and as a result, the installation of the ferrous materials may include adding additional material to at least a portion of the base to facilitate coupling to other components of the wearable device housing.

As described elsewhere, the base may be utilized to arrange a plurality of sensors within a wearable device. Various locations of the sensors may be particularly selected based on the sensor type, as well as for size and space constraints. In embodiments, the base may also act as an electrode for one or more of the sensors utilized by the wearable device. For example, as noted above, the base may be thermally and/or electrically conductive. As a result, thermal signals from the base may be transmitted to one or more temperature sensors. Furthermore, electrical signals may also be transmitted via the base. Moreover, in embodiments, the openings may enable optical sensing through the base. As a result, the base may be utilized to enable a plurality of different type so sensors to obtain physical information from a user having the wearable device.

Figure 12:
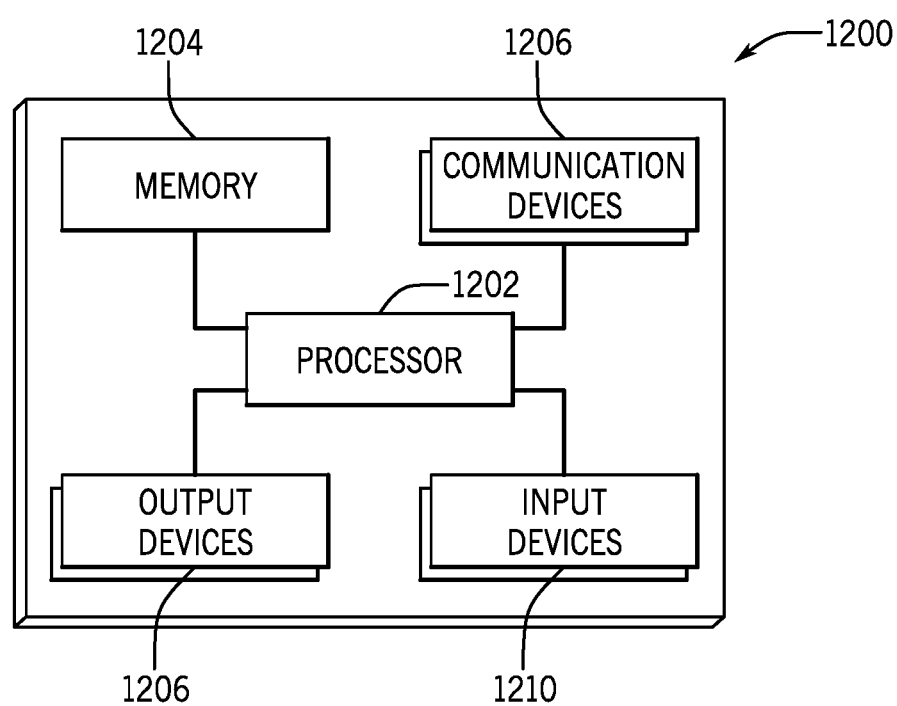
FIG. 12 illustrates a set of basic components of one or more devices of the present disclosure, in accordance with various embodiments of the present disclosure.

FIG. 12 illustrates a set of basic components 1200 of one or more devices of the present disclosure, in accordance with various embodiments of the present disclosure. In this example, the device includes at least one processor 1202 for executing instructions that can be stored in a memory device or element 1204. As would be apparent to one of ordinary skill in the art, the device can include many types of memory, data storage or computer-readable media, such as a first data storage for program instructions for execution by the at least one processor 1202, the same or separate storage can be used for images or data, a removable memory can be available for sharing information with other devices, and any number of communication approaches can be available for sharing with other devices. The device may include at least one type of output device 1206, such as a touch screen, electronic ink (e-ink), organic light emitting diode (OLED) or liquid crystal display (LCD), although devices such as servers might convey information via other means, such as through a system of lights and data transmissions. The device typically will include one or more networking device 1208, such as a port, network interface card, or wireless transceiver that enables communication over at least one network. The device can include at least one input device 1210 able to receive conventional input from a user. This conventional input can include, for example, a push button, touch pad, touch screen, wheel, joystick, keyboard, mouse, trackball, keypad or any other such device or element whereby a user can input a command to the device. These I/O devices could even be connected by a wireless infrared or Bluetooth or other link as well in some embodiments. In some embodiments, however, such a device might not include any buttons at all and might be controlled only through a combination of visual and audio commands such that a user can control the device without having to be in contact with the device.

As discussed, different approaches can be implemented in various environments in accordance with the described embodiments. As will be appreciated, although a Web-based environment is used for purposes of explanation in several examples presented herein, different environments may be used, as appropriate, to implement various embodiments. The system includes an electronic client device, which can include any appropriate device operable to send and receive requests, messages or information over an appropriate network and convey information back to a user of the device. Examples of such client devices include personal computers, cell phones, handheld messaging devices, laptop computers, set-top boxes, personal data assistants, electronic book readers and the like. The network can include any appropriate network, including an intranet, the Internet, a cellular network, a local area network or any other such network or combination thereof. Components used for such a system can depend at least in part upon the type of network and/or environment selected. Protocols and components for communicating via such a network are well known and will not be discussed herein in detail. Communication over the network can be enabled via wired or wireless connections and combinations thereof. In this example, the network includes the Internet, as the environment includes a Web server for receiving requests and serving content in response thereto, although for other networks, an alternative device serving a similar purpose could be used, as would be apparent to one of ordinary skill in the art.

The illustrative environment includes at least one application server and a data store. It should be understood that there can be several application servers, layers or other elements, processes or components, which may be chained or otherwise configured, which can interact to perform tasks such as obtaining data from an appropriate data store. As used herein, the term "data store" refers to any device or combination of devices capable of storing, accessing and retrieving data, which may include any combination and number of data servers, databases, data storage devices and data storage media, in any standard, distributed or clustered environment. The application server can include any appropriate hardware and software for integrating with the data store as needed to execute aspects of one or more applications for the client device and handling a majority of the data access and business logic for an application.

The application server provides access control services in cooperation with the data store and is able to generate content such as text, graphics, audio and/or video to be transferred to the user, which may be served to the user by the Web server in the form of HTML, XML or another appropriate structured language in this example. The handling of all requests and responses, as well as the delivery of content between the client device and the application server, can be handled by the Web server. It should be understood that the Web and application servers are not required and are merely example components, as structured code discussed herein can be executed on any appropriate device or host machine as discussed elsewhere herein. The data store can include several separate data tables, databases or other data storage mechanisms and media for storing data relating to a particular aspect. For example, the data store illustrated includes mechanisms for storing content (e.g., production data) and user information, which can be used to serve content for the production side. The data store is also shown to include a mechanism for storing log or session data. It should be understood that there can be many other aspects that may need to be stored in the data store, such as page image information and access rights information, which can be stored in any of the above listed mechanisms as appropriate or in additional mechanisms in the data store. The data store is operable, through logic associated therewith, to receive instructions from the application server and obtain, update or otherwise process data in response thereto. In one example, a user might submit a search request for a certain type of item. In this case, the data store might access the user information to verify the identity of the user and can access the catalog detail information to obtain information about items of that type. The information can then be returned to the user, such as in a results listing on a Web page that the user is able to view via a browser on the user device. Information for a particular item of interest can be viewed in a dedicated page or window of the browser.

Each server typically will include an operating system that provides executable program instructions for the general administration and operation of that server and typically will include computer-readable medium storing instructions that, when executed by a processor of the server, allow the server to perform its intended functions. Suitable implementations for the operating system and general functionality of the servers are known or commercially available and are readily implemented by persons having ordinary skill in the art, particularly in light of the disclosure herein.

The environment in one embodiment is a distributed computing environment utilizing several computer systems and components that are interconnected via communication links, using one or more computer networks or direct connections. However, it will be appreciated by those of ordinary skill in the art that such a system could operate equally well in a system having fewer or a greater number of components than are illustrated. Thus, the depiction of the systems herein should be taken as being illustrative in nature and not limiting to the scope of the disclosure.

The various embodiments can be further implemented in a wide variety of operating environments, which in some cases can include one or more user computers or computing devices which can be used to operate any of a number of applications. User or client devices can include any of a number of general purpose personal computers, such as desktop or notebook computers running a standard operating system, as well as cellular, wireless and handheld devices running mobile software and capable of supporting a number of networking and messaging protocols. Devices capable of generating events or requests can also include wearable computers (e.g., smart watches or glasses), VR headsets, Internet of Things (IoT) devices, voice command recognition systems, and the like. Such a system can also include a number of workstations running any of a variety of commercially-available operating systems and other known applications for purposes such as development and database management. These devices can also include other electronic devices, such as dummy terminals, thin-clients, gaming systems and other devices capable of communicating via a network.

Most embodiments utilize at least one network that would be familiar to those skilled in the art for supporting communications using any of a variety of commercially-available protocols, such as TCP/IP, FTP, UPnP, NFS, and CIFS. The network can be, for example, a local area network, a wide-area network, a virtual private network, the Internet, an intranet, an extranet, a public switched telephone network, an infrared network, a wireless network and any combination thereof.

In embodiments utilizing a Web server, the Web server can run any of a variety of server or mid-tier applications, including HTTP servers, FTP servers, CGI servers, data servers, Java servers and business application servers. The server(s) may also be capable of executing programs or scripts in response requests from user devices, such as by executing one or more Web applications that may be implemented as one or more scripts or programs written in any programming language, such as Java®, C, C# or C++ or any scripting language, such as Perl, Python or TCL, as well as combinations thereof. The server(s) may also include database servers, including without limitation those commercially available from Oracle®, Microsoft®, Sybase® and IBM® as well as open-source servers such as MySQL, Postgres, SQLite, MongoDB, and any other server capable of storing, retrieving and accessing structured or unstructured data. Database servers may include table-based servers, document-based servers, unstructured servers, relational servers, non-relational servers or combinations of these and/or other database servers.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network (SAN) familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit (CPU), at least one input device (e.g., a mouse, keyboard, controller, touch-sensitive display element or keypad) and at least one output device (e.g., a display device, printer or speaker). Such a system may also include one or more storage devices, such as disk drives, optical storage devices and solid-state storage devices such as random access memory (RAM) or read-only memory (ROM), as well as removable media devices, memory cards, flash cards, etc.

Such devices can also include a computer-readable storage media reader, a communications device (e.g., a modem, a network card (wireless or wired), an infrared communication device) and working memory as described above. The computer-readable storage media reader can be connected with, or configured to receive, a computer-readable storage medium representing remote, local, fixed and/or removable storage devices as well as storage media for temporarily and/or more permanently containing, storing, transmitting and retrieving computer-readable information. The system and various devices also typically will include a number of software applications, modules, services or other elements located within at least one working memory device, including an operating system and application programs such as a client application or Web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Storage media and other non-transitory computer readable media for containing code, or portions of code, can include any appropriate media known or used in the art, such as but not limited to volatile and non-volatile, removable and non-removable media implemented in any method or technology for storage of information such as computer readable instructions, data structures, program modules or other data, including RAM, ROM, EEPROM, flash memory or other memory technology, CD-ROM, digital versatile disk (DVD) or other optical storage, magnetic cassettes, magnetic tape, magnetic disk storage or other magnetic storage devices or any other medium which can be used to store the desired information and which can be accessed by a system device. Based on the disclosure and teachings provided herein, a person of ordinary skill in the art will appreciate other ways and/or methods to implement the various embodiments.

While various embodiments of the invention have been described above, it should be understood that they have been presented by way of example only, and not by way of limitation. Likewise, the various diagrams may depict an example architectural or other configuration for the disclosure, which is done to aid in understanding the features and functionality that can be included in the disclosure. The disclosure is not restricted to the illustrated example architectures or configurations, but can be implemented using a variety of alternative architectures and configurations. Additionally, although the disclosure is described above in terms of various exemplary embodiments and implementations, it should be understood that the various features and functionality described in one or more of the individual embodiments are not limited in their applicability to the particular embodiment with which they are described. They instead can be applied, alone or in some combination, to one or more of the other embodiments of the disclosure, whether or not such embodiments are described, and whether or not such features are presented as being a part of a described embodiment. Thus the breadth and scope of the present disclosure should not be limited by any of the above-described exemplary embodiments.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

All of the features disclosed in this specification (including any accompanying exhibits, claims, abstract and drawings), and/or all of the steps of any method or process so disclosed, may be combined in any combination, except combinations where at least some of such features and/or steps are mutually exclusive. The disclosure is not restricted to the details of any foregoing embodiments. The disclosure extends to any novel one, or any novel combination, of the features disclosed in this specification (including any accompanying claims, abstract and drawings), or to any novel one, or any novel combination, of the steps of any method or process so disclosed.

Various modifications to the implementations described in this disclosure may be readily apparent to those skilled in the art, and the generic principles defined herein may be applied to other implementations without departing from the spirit or scope of this disclosure. Thus, the disclosure is not intended to be limited to the implementations shown herein, but is to be accorded the widest scope consistent with the principles and features disclosed herein. Certain embodiments of the disclosure are encompassed in the claim set listed below or presented in the future.

What is claimed is:

1. A system forming at least a portion of a wearable device, the system comprising:
    an electrically and thermally conductive base plate forming at least a portion of the wearable device, the base plate having a first surface and a second surface, the first surface forming at least a part of an exterior of the wearable device and the second surface being at least partially enclosed within the wearable device, the base plate defining a plurality of openings extending through a thickness of the base plate from the first surface to the second surface, each of the plurality of openings positioned closer to a center of the base plate than a periphery of the base plate, the second surface of the base plate defining a plurality of recesses, the entirety of each of the recesses being positioned farther from the center of the base plate than each of the openings;
    a first sensor arranged in a first recess of the plurality of recesses, the first recess in direct contact with the base plate, the first sensor configured to receive at least one of an electrical or thermal signal from the first surface of the base plate as an input for measuring one or more physical properties of a user of the wearable device such that the base plate serves as a continuous conductive contact for the first sensor;
    a pane installed within each opening of the plurality of openings, the pane being at least semi-transparent enabling optical signal transmission through the pane, wherein the pane includes a pane thickness less than the thickness of the base plate; and
    an optical sensor arranged in at least one of the plurality of openings such that a respective pane within the at least one of the plurality of openings is between the optical sensor and the first surface, the optical sensor receiving an optical signal through the pane.

2. The system of claim 1, further comprising:
    at least two additional sensors, wherein the first sensor and the at least two additional sensors each utilize a different method for determining the one or more physical properties of the user of the wearable device.

3. The system of claim 1, wherein the first sensor comprises a temperature sensor, and wherein the base plate transmits a temperature of at least a portion of the base plate to the temperature sensor.

4. The system of claim 1, wherein the base plate is further coupled to at least two sensors, the base plate being an electrode for both of the at least two sensors, wherein at least one of the at least two sensors is utilized for electrocardiogram.

5. The system of claim 1, wherein the pane and the base plate are formed from a different material, the pane having a substantially equal coefficient of thermal expansion as the base.

6. A system for forming at least a portion of a wearable device, comprising:
    a base plate forming a bottom portion of a wearable device, the base plate being electrically and thermally conductive, the base plate having a first surface and a second surface, the first surface forming at least a part of an exterior of the wearable device, the second surface being at least partially enclosed within the wearable device, the base plate defining a plurality of openings, each of the plurality of openings extending through a thickness of the base plate from the first surface to the second surface, each of the plurality of openings positioned closer to a center of the base plate than a periphery of the base plate, the second surface of the base plate defining a plurality of recesses, the entirety of each of the recesses being positioned farther from the center of the base plate than each of the openings;
    a plurality of charging pins extending through a thickness of the base plate, the charging pins extending normal to the second surface of the base plate by a first distance;
    a plurality of panes, wherein a pane of the plurality of panes is arranged within a respective opening of the plurality of openings, the plurality of panes being at least semi-transparent and formed from a material different than a material of the base plate; and
    a plurality of sensors coupled to the base plate, the plurality of sensors comprising at least three sensors, each sensor of the plurality of sensors having a different detection signal, wherein at least two of the at least three sensors are in direct contact with the base plate and utilize the base plate as an electrode configured to provide a continuous conductive contact for at least one of an electrical or a thermal signal to the at least two of the at least three sensors as an input for measuring one or more physical properties of a user of the wearable device, wherein a first sensor of the at least two sensors is arranged within a first recess of the plurality of recesses.

7. The system of claim 6, further comprising:

a plurality of sleeves wherein a sleeve of the plurality of sleeves is positioned around a respective charging pin of the plurality of charging pins, the plurality of sleeves being coupled directly to the base plate, wherein the plurality of sleeves are formed from a different material the plurality of charging pins.

8. The system of claim 6, further comprising:

a light blocking assembly arranged to be light tight to apertures surrounding the plurality of charging pins.

9. The system of claim 6, wherein at least one sensor of the plurality of sensors is a temperature sensor, the temperature sensor thermally coupled to the base plate.

10. The system of claim 6, wherein the plurality of openings are arranged symmetrically about at least one of a horizontal axis or a vertical axis.

11. The system of claim 6, wherein at least one sensor of the plurality of sensors is an optical sensor arranged over at least one opening of the plurality of openings, the optical sensor receiving a signal through the respective pane arranged within the at least one opening.

12. The system of claim 6, wherein at least one opening of the plurality of openings is substantially pilled shaped, the at least one openings having a plurality of curved edges.

13. The system of claim 6, further comprising:

at least one ferrous insert arranged on the base plate, wherein the base plate is formed from a non-ferrous material.

14. The system of claim 6, further comprising:

a pin extending normal from the first surface, the pin being at least part of one sensor of the plurality of sensors.

15. A method for forming at least a portion of a wearable device, comprising:

forming a base plate from a first material, the first material being both electrically and thermally conductive;

forming a plurality of openings in the base plate, each of the openings extending from an inside surface of the base plate to an outside surface of the base plate, each of the openings positioned closer to a center of the base plate than a periphery of the base plate;

installing a pane into respective openings of the plurality of openings, the pane formed from a second material different than the first material, the second material being at least semi-transparent and having a thickness less than the thickness of the first material; and forming a plurality of recesses in the inside surface of the base plate, the entirety of each of the recesses being positioned farther from the center of the base plate than each of the openings;

forming the base plate as an electrode for at least one sensor in the wearable device, wherein the at least one sensor is in direct contact with the base plate, the base plate configured to provide a continuous conductive contact between a first surface of the base plate and the at least one sensor.

16. The method of claim 15, further comprising:

thermally coupling the at least one sensor to the base plate.

17. The method of claim 15, further comprising:

coupling at least one ferrous insert to the base plate, the at least one ferrous insert formed from a third material different than the first material.

18. The method of claim 15, further comprising:

installing a least two sensors on the base plate, each of the two sensors using the base plate as an electrode.

19. The system of claim 1, wherein a depth of a second recess of the plurality of recesses is different than a depth of the first recess.

20. The system of claim 1, further comprising:

a magnet positioned in a second recess of the plurality of recesses, the magnet configured to magnetically couple the base plate to a charger.

* * * * *